US00PP35509P2

(12) United States Plant Patent
Hartman

(10) Patent No.: US PP35,509 P2
(45) Date of Patent: Nov. 28, 2023

(54) ***CALADIUM* PLANT NAMED 'THAI STR OF17-1082'**

(50) Latin Name: ***Caladium* X *hortulanum***
Varietal Denomination: THAI STR OF17-1082

(71) Applicant: Robert Dale Hartman, Lake Placid, FL (US)

(72) Inventor: Robert Dale Hartman, Lake Placid, FL (US)

( * ) Notice: Subject to any disclaimer, the term of this patent is extended or adjusted under 35 U.S.C. 154(b) by 0 days.

(21) Appl. No.: 18/121,521

(22) Filed: Mar. 14, 2023

(51) Int. Cl.
*A01H 5/12* (2018.01)
*A01H 6/10* (2018.01)

(52) U.S. Cl.
USPC ..... Plt./373

(58) Field of Classification Search
USPC ..... Plt./373
See application file for complete search history.

*Primary Examiner* — Susan McCormick Ewoldt
(74) *Attorney, Agent, or Firm* — C. Anne Whealy

(57) ABSTRACT

A new and distinct cultivar of *Caladium* plant named 'THAI STR OF17-1082', characterized by its intermediate in height and upright to mounding plant habit; dense, leafy and bushy appearance; moderately vigorous growth habit and rapid growth rate; lance-type leaves that are very dark green with a dark reddish brown cast appearing close to black in color; dark colored petioles that are close to black in color; and tolerance to full sunlight conditions.

4 Drawing Sheets

Figure 1:
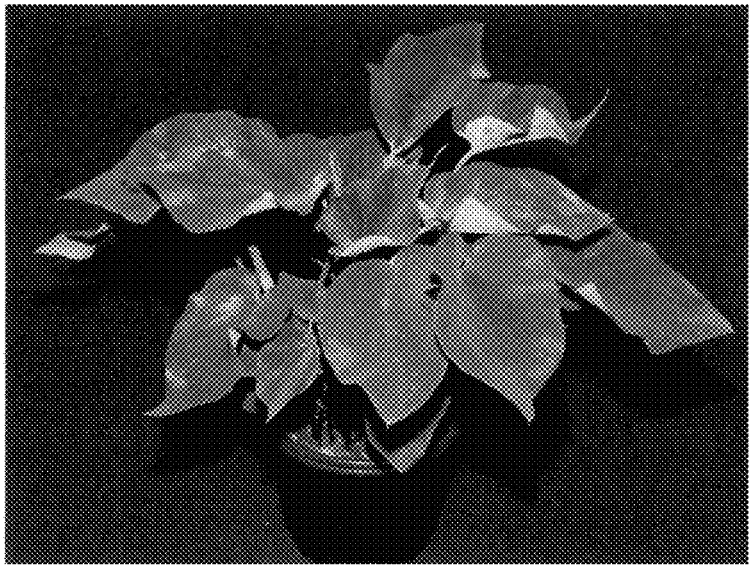

Botanical designation: *Caladium* X *hortulanum.*
Cultivar denomination: 'THAI STR OF17-1082'.

STATEMENT REGARDING PRIOR DISCLOSURES BY INVENTOR/APPLICANT

The Inventor/Applicant asserts that no publications nor advertisements relating to sales, offers for sale or public distribution occurred more than one year prior to the effective filing date of this application. Any information about the claimed plant would have been obtained from a direct or indirect disclosure from the Inventor/Applicant. Inventor/Applicant claims a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Caladium* plant, botanically known as *Caladium* X *hortulanum*, commercially referred to as a lance leaf-type *Caladium* and hereinafter referred to by the name 'THAI STR OF17-1082'.

The objective of the Inventor's breeding program is to create new *Caladium* plants that have uniform plant habit, exceptional container and garden performance and attractive and unique leaf coloration.

The new *Caladium* plant originated from a cross-pollination made by the Inventor in April, 2016 in Avon Park, Fla. of *Caladium* X *hortulanum* 'Florida Red Ruffles', disclosed in U.S. Plant Pat. No. 13,136, as the female, or seed, parent with *Caladium* X *hortulanum* 'Toasted Bronze', not patented, as the male, or pollen, parent. The new *Caladium* plant was discovered and selected by the Inventor as a single plant within the progeny of the stated cross-pollination in a controlled outdoor nursery environment in Avon Park, Fla. in September, 2017.

Asexual reproduction of the new *Caladium* plant by "chipping" the tubers (cutting the tuber into segments with each segment containing an axillary bud and tuber cortical tissue) in a controlled outdoor nursery environment in Zolfo Springs, Fla. since April, 2018 has shown that the unique features of this new *Caladium* plant are stable and reproduced true to type in successive generations of asexual reproduction.

SUMMARY OF THE INVENTION

Plants of the new *Caladium* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'THAI STR OF17-1082'. These characteristics in combination distinguish 'THAI STR OF17-1082' as a new and distinct *Caladium* plant:

1. Intermediate in height and upright to mounding plant habit; dense, leafy and bushy appearance.
2. Moderately vigorous growth habit and rapid growth rate.
3. Lance-type leaves that are very dark green with a dark reddish brown cast appearing close to black in color.
4. Dark colored petioles that are close to black in color.
5. Tolerant to full sunlight conditions.

Plants of the new *Caladium* differ primarily from plants of the female parent, 'Florida Red Ruffles', in the following characteristics:

1. Plants of the new *Caladium* are intermediate in height whereas plants of 'Florida Red Ruffles' are short in height.
2. Leaves of plants of the new *Caladium* very dark green with a dark reddish brown cast appearing close to black in color are whereas leaves of plants of 'Florida Red Ruffles' have dark red-colored venation and intervenous areas and green-colored borders.

3. Plants of the new *Caladium* have dark colored petioles that are close to black in color whereas plants of 'Florida Red Ruffles' have petioles that close to black in color with tannish pink-colored stripes.

Plants of the new *Caladium* differ primarily from plants of the male parent, 'Toasted Bronze', in the following characteristics:

1. Plants of the new *Caladium* are intermediate in height whereas plants of 'Toasted Bronze' are short in height.
2. Plants of the new *Caladium* are more vigorous than plants of 'Toasted Bronze'.
3. Leaves of plants of the new *Caladium* very dark green with a dark reddish brown cast appearing close to black in color whereas leaves of plants of 'Toasted Bronze' are reddish bronze in color with darker-colored venation.

Plants of the new *Caladium* can be compared to plants of *Caladium* X *hortulanum* 'Burning Heart', disclosed in U.S. Plant Pat. No. 27,071. In side-by-side comparisons, plants of the new *Caladium* differ primarily from plants of 'Burning Heart' in the following characteristics:

1. Leaves of plants of the new *Caladium* are lance types whereas leaves of plants of 'Burning Heart' are fancy types.
2. Leaves of plants of the new *Caladium* are very dark green with a dark reddish brown cast appearing close to black in color whereas leaves of plants of 'Burning Heart' are bronze red in color with contrasting salmon orange-colored spots and dark red bronze-colored venation.
3. Leaf petioles of plants of the new *Caladium* are close to black in color whereas leaf petioles of plants of 'Burning Heart' are tannish green to tannish pink in color.

Plants of the new *Caladium* can also be compared to plants of *Caladium* X *hortulanum* 'RUF 1522-3', disclosed in U.S. Plant Pat. No. 33,615. In side-by-side comparisons, plants of the new *Caladium* differ primarily from plants of 'RUF 1522-3' in the following characteristics:

1. Plants of the new *Caladium* are intermediate in height whereas plants of 'RUF 1522-3' are short to intermediate in height.
2. Leaves of plants of the new *Caladium* are narrower than leaves of plants of 'RUF 1522-3'.
3. Leaves of plants of the new *Caladium* are very dark green with a dark reddish brown cast appearing close to black in color whereas leaves of plants of 'RUF 1522-3' are dark red in color with dark green-colored margins.
4. Leaf petioles of plants of the new *Caladium* are close to black in color whereas leaf petioles of plants of 'RUF 1522-3' are tannish pink in color with greenish brown-colored stripes, streaks, stippling and tessellations.

BRIEF DESCRIPTION OF THE PHOTOGRAPHS

The accompanying photographs illustrate the overall appearance of the new *Caladium* plant showing the colors as true as it is reasonably possible to obtain in colored reproductions of this type. Colors in the photographs may differ slightly from the color values cited in the detailed botanical description which accurately describe the colors of the new *Caladium* plant.

The photograph on the first sheet (FIG. 1) is a side perspective view of a typical plant of 'THAI STR OF17-1082' grown in a container that has had its tuber de-eyed prior to planting.

Figure 2:
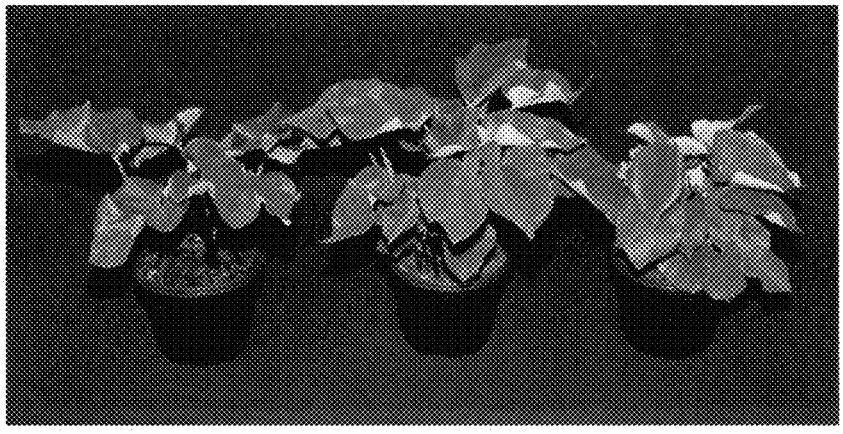

The photograph at the top of the second sheet (FIG. 2) is side perspective view of typical plants of the female parent, 'Florida Red Ruffles' (right), 'THAI STR OF17-1082' (center) and the male parent, 'Toasted Bronze' (left).

Figure 3:
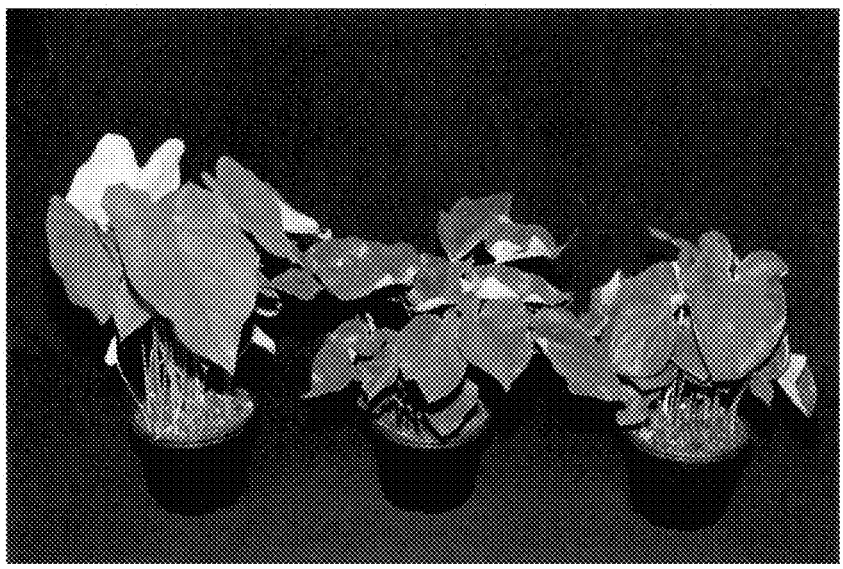

The photograph at the bottom of the second sheet (FIG. 3) is side perspective view of typical plants of 'Burning Heart' (left), 'THAI STR OF17-1082' (center) and 'RUF 1522-3' (right).

Figure 4:
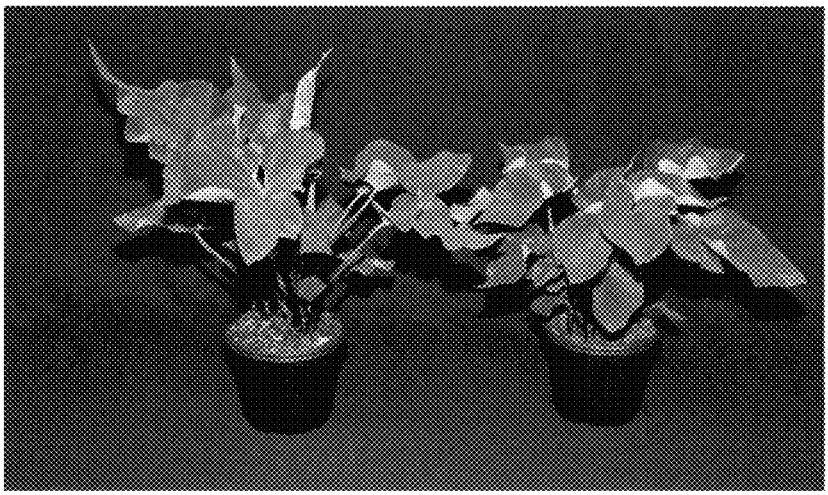

The photograph at the top of the third sheet (FIG. 4) is a comparison view of typical plants of 'THAI STR OF17-1082' grown in containers, the plant on the left has not had its tuber de-eyed and the plant on the right has had its tuber de-eyed prior to planting.

Figure 5:
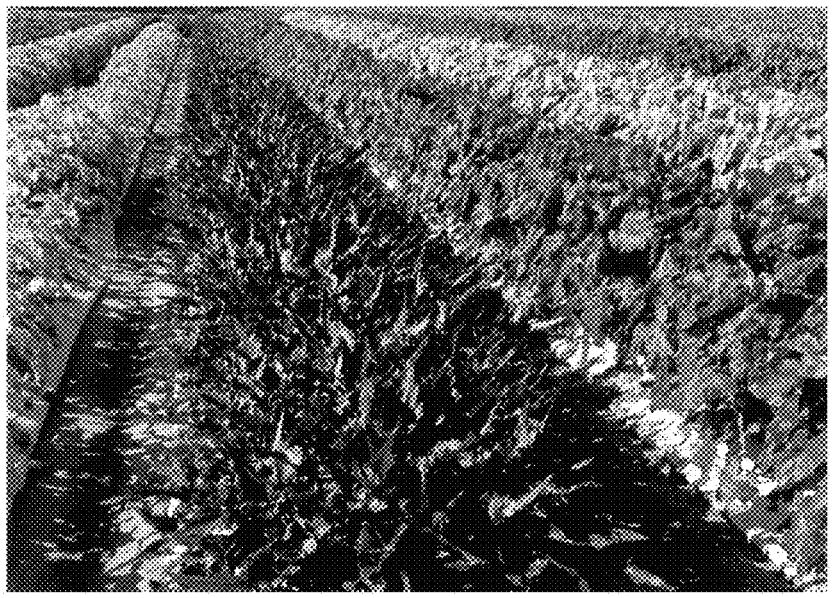

The photograph at the bottom of the third sheet (FIG. 5) is a side perspective view of typical plants of 'THAI STR OF17-1082' grown in an open production field.

Figure 6:
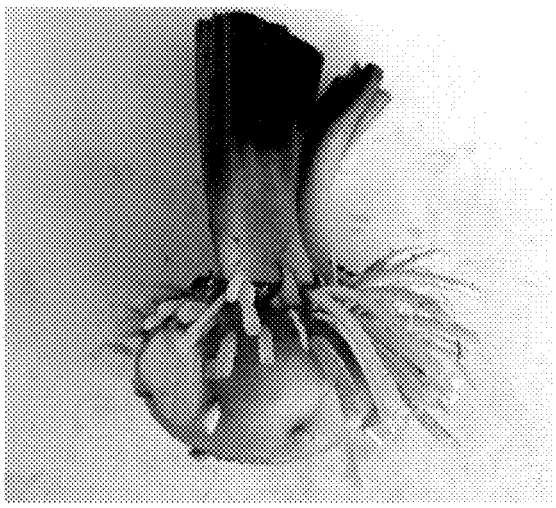

The photograph at the top of the fourth sheet (FIG. 6) is a close-up view of typical freshly-harvested tubers with roots and leaf petioles of 'THAI STR OF17-1082'.

Figure 7:
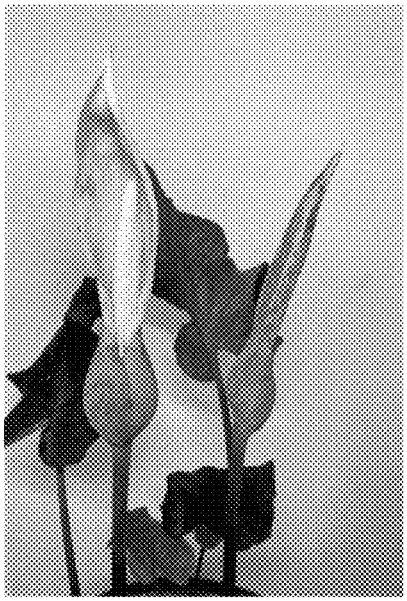

The photograph at the bottom of the fourth sheet (FIG. 7) is a close-up view of a typical flowering plant of 'THAI STR OF17-1082'.

DETAILED BOTANICAL DESCRIPTION

The aforementioned photographs and following observations and measurements describe plants grown in 15-cm containers in a polypropylene-covered shade house (30% light reduction) in Avon Park, Fla. and plants grown in ground beds under full sunlight conditions in an outdoor nursery in Crewsville, Fla. The plants were grown under cultural practices typical of commercial shade house and outdoor nursery production. During the production of the shade house-grown plants, day temperatures ranged from about 28 C to 33 C, night temperatures ranged from about 22 C to 25 C and light levels were about 1,300 μmol. During the production of the outdoor nursery-grown plants, day temperatures ranged from about 29 C to 35 C, night temperatures ranged from about 23 C to 26 C and full sunlight conditions. Plants grown in the shade house were nine weeks old and plants grown in the outdoor nursery were five months old when the photographs and the detailed description were taken. In the following description, color references are made to The Royal Horticultural Society Colour Chart, 2001 and 2015 Editions, except where general terms of ordinary dictionary significance are used.

Botanical classification: *Caladium* X *hortulanum* 'THAI STR OF17-1082'.

Parentage:

*Female, or seed, parent.*—*Caladium* X *hortulanum* 'Florida Red Ruffles', disclosed in U.S. Plant Pat. No. 13,136.

*Male, or pollen, parent.*—*Caladium* X *hortulanum* 'Toasted Bronze', not patented.

Propagation:

*Type*.—By "chipping" the tubers.

*Time to initiate roots, summer*.—About seven to ten days at temperatures about 32 C.

*Time to initiate roots, winter*.—About two to three weeks at temperatures about 24 C.

*Tuber description* (*outdoor nursery-grown plants*).—Appearance: Multi-segmented, clumping and branched tubers; individual segments are elliptic to irregular in shape. Height: About 3.3 cm to 3.5 cm. Diameter: About 5.3 cm to 6 cm. Segment height: About 2.2 cm. Segment diameter: About 1.7 cm. Axillary bud shape: Roughly triangular. Axillary bud height: About 5 mm. Axillary bud width: About 7 mm. Texture: Thick, starchy; somewhat brittle. Color: Periderm, freshly-harvested: Close to N177B. Periderm, dried: Close to 200A. Epidermis: Close to 49D becoming closer to N170D with subsequent development. Cortical tissue: Close to 4D. Axillary buds: Close to 38C and 49D. Root description: Thick, fleshy contractile roots with few lateral branches; color, close to NN155D; actual color of the roots is dependent on substrate composition, water quality, fertilizer type and formulation, substrate temperature and physiological age of roots. Rooting density: Moderately dense.

Plant description:

*Plant type*.—Herbaceous perennial; suitable as a potted plant in containers 15-cm to 25-cm and suitable as a landscape plant in shaded and full sunlight areas.

*Plant and growth habit*.—Intermediate in height and upright to mounding plant habit; plants grown from tubers that have been de-eyed are more mounded than plants grown from tubers that have not been de-eyed; dense, leafy and bushy appearance; moderately vigorous growth habit and rapid growth rate; potted plants finish in saleable form in about nine weeks after planting tubers; leaf petioles and leaves arise from one or more growing points on tubers; leaf petioles initially upright and leaning outwardly with development.

*Plant height, from soil level to top of foliar plane, shade house-grown potted plants*.—When de-eyed, about 33 cm to 40 cm; when not de-eyed, about 43 cm.

*Plant height, from soil level to top of floral plane, shade house-grown potted plants*.—About 36 cm.

*Plant diameter, shade house-grown potted plants*.—When de-eyed, about 37 cm; when not de-eyed, about 50 cm to 52 cm.

*Number of shoots per plant, shade house-grown potted plants, tubers not de-eyed*.—About one to three develop per #1 tuber.

*Number of shoots per plant, shade house-grown potted plants, tubers de-eyed*.—About five to nine develop per #1 tuber.

*Cataphylls, shade house-grown potted plants*.—Length: About 5.2 cm to 7.5 cm. Width: About 1 cm to 1.3 cm. Shape: Lanceolate to triangular. Apex: Variable, acute to slightly emarginate. Base: Sheathing the stem. Texture, outer and inner surfaces: Smooth, glabrous. Color, outer surface: Close to 203A; color becoming closer to 200B and 203A with subsequent development. Color, inner surface: Close to N155C and N187D flushed and streaked with close to 200B; edges, close to N200A; colors and color patterns visible from outer surface.

Leaf description:

*Arrangement and type*.—Alternate; simple; lance-type.

*Length, shade house-grown potted plants*.—When de-eyed, about 15.5 cm to 19.5 cm; when not de-eyed, about 19.5 cm to 24.5 cm.

*Width, shade house-grown potted plants*.—When de-eyed, about 8 cm to 9 cm and flattened, about 10 cm to 11 cm; when not de-eyed, about 10 cm to 12.8 cm and flattened, about 14.3 cm to 18 cm.

*Shape*.—Ovate to lanceolate; with development, cupped and somewhat conduplicate.

*Apex*.—Acute to acuminate.

*Base*.—Sagittate-peltate; cordate.

*Margin*.—Entire; moderately flat to wavy with broad undulations.

*Texture and luster, upper surface*.—Smooth, glabrous; dull to glossy and slightly glaucous; medium in thickness and somewhat rigid.

*Texture and luster, lower surface*.—Smooth, glabrous; glaucous and dull in sheen.

*Venation pattern*.—Pinnate and palmate.

*Color, shade house-grown potted de-eyed plants*.—Developing and fully expanded leaves, upper surface: Background color: Darker than 147A and NN137A; variably flushed and blotched with close to N200A tinged with close to 183A. Margins: Close to 183A and 183B; edges, close to 187A. Basal notch: Close to 147C, 147D and 155C; edges, close to 187A; at leaf petiole junction, close to N186A and N186C. Midvein and lateral venation: Close to 203A and N186A; areas surrounding venation, close to 203A and N186A. Developing and fully expanded leaves, lower surface: Background color: Close to 189C, 189D, 191A and 195B; variably flushed and mottled with close to N186A tinged with close to N186C. Margins: Close to 191A variably flushed and mottled with close to N186A tinged with close to N186C; edges, close to 187A. Basal notch: Close to 187A. Midvein: Close to 183A and 200B. Primary veins: Close to 183A, 200B and N170D.

*Petioles*.—Aspect: Initially upright and straight, and slightly outwardly leaning with development; flexible. Length, shade house-grown de-eyed potted plants: About 18.2 cm to 27 cm. Length, shade house-grown not de-eyed potted plants: About 24 cm to 33 cm. Diameter, distally, shade house-grown de-eyed potted plants: About 3 mm to 4 mm. Diameter, distally, shade house-grown not de-eyed potted plants: About 4.5 mm to 6 mm. Diameter, proximally, shade house-grown de-eyed potted plants: About 6.5 mm to 8 mm. Diameter, proximally, shade house-grown not de-eyed potted plants: About 7 mm to 11 mm. Texture and luster: Smooth, glabrous; glossy. Color, shade house-grown potted plants: Close to 203A and N200A; just below the leaf junction, close to 203A. Wing length, shade house-grown de-eyed potted plants: About 5.5 cm to 8.5 cm. Wing length, shade house-grown not de-eyed potted plants: About 5.5 cm to 12.5 cm. Wing diameter, shade house-grown de-eyed potted plants: About 6 mm to 9 mm. Wing diameter, shade house-grown not de-eyed potted plants: About 8.5 mm to 10 mm. Texture and luster, inner and outer surfaces: Smooth, glabrous; slightly glossy. Wing color, shade house-grown potted plants: Outer surface: Close to 203A or N155C with marbling, close to 203A. Inner surface: Close to N187D and N155C; center, flushed and streaked with close to 200B; edges, close to N200A; colors and patterns on the outer surface are visible on the inner surface.

Inflorescence description:

*Inflorescence arrangement*.—Upright hooded spathes surrounding a columnar spadix borne on an upright scape; spadix with sessile, simple female and male flowers separated into two zones; female flowers develop on the proximal one-third of the spadix; male flowers develop on the distal two-thirds of the spadix; sterile flowers develop at junction of female and male flower zones; near this junction, the spathe constricts and surrounds and encloses the female flowers; spathe open and cupped around male flowers.

*Fragrance*.—Night-fragrant; jasmine-like with mint/camphor note.

*Natural flowering season and flower longevity*.—Plants of the new *Caladium* typically flower during the spring and summer in central Florida; flowers develop about four weeks after growth commences; inflorescences last about three days before fading; inflorescences persistent.

*Spathe*.—Length, overall: About 14.8 cm. Length, distal open portion: About 10 cm. Length, proximal closed portion: About 4.8 cm. Width, distal open portion: About 2.9 cm. Depth, distal open portion: About 1.5 cm. Width, at constriction: About 1.5 cm. Width, proximal closed portion: About 3.1 cm. Shape, open portion: Narrowly elliptic to obovate. Apex: Acute. Base: Acute to somewhat obtuse. Margin: Entire; proximally, may be split. Texture and luster, front surface: Smooth, glabrous; dull sheen. Texture and luster, rear surface: Distally, smooth, glabrous with a dull sheen; proximally, smooth, glabrous, slightly glaucous. Color, front surface: Distal open portion: Close to 159D tinged with close to N170D and 182D; with subsequent development, becoming closer to 199A. Proximal closed portion: Close to 148C and 148D; towards the base, flushed with close to 187A and N186C; color does not change with subsequent development. Color, rear surface: Distal open portion: Close to 158A; center, tinged with close to 160D; margin, faintly tinged with close to 182D; blotches, veins and streaks, close to 200B tinged with close to N186C; color does not change with subsequent development. Proximal closed portion: Close to 147B with blotches, close to 202A; color does not change with subsequent development.

*Spadix*.—Length, overall: About 10 cm. Length, male flower zone: About 5.7 cm. Length, sterile zone: About 2 cm. Length, female flower zone: About 2.3 cm. Diameter, male flower zone: About 1 cm. Diameter, sterile flower zone: About 7 mm. Diameter, female flower zone: About 1.2 mm. Shape: Columnar, spindle-shaped. Apex: Acute to rounded. Base: Obtuse. Aspect: Upright. Color, mature, male zone: Close to 158D tinged with close to 18D. Color, mature, sterile zone: Close to 159C and 159D. Color, mature, female zone: Close to 159D and 158B. Male flowers: Quantity per spadix: About 320. Shape: Obovate. Height: About 2.5 mm. Diameter: About 3 mm. Pollen amount: None observed. Female flowers: Quantity per spadix: About 260. Shape: Ovate to elliptic. Height: About 3.5 mm. Diameter: About 3.5 mm. Stigma color: Close to 159D. Ovary color: Close to 158B.

*Scapes*.—Length: About 26 cm. Diameter: About 6 mm. Strength: Sturdy; somewhat flexible. Aspect: Mostly erect, straight. Texture and luster: Smooth, glabrous; glossy; distally, glaucous. Color: Close to 202A tinged with close to N186A.

*Seeds and fruits*.—To date, seed and fruit development have not been observed on plants of the new *Caladium*.

Pathogen tolerance/resistance: Plants of the new *Caladium* have been observed to have average tolerance to *Pythium* Root Rot and average tolerance to *Xanthomonas* Leaf Spot. Plants of the new *Caladium* have not been observed to have tolerance/resistance to other pathogens common to *Caladium* plants.

Temperature tolerance: Plants of the new *Caladium* have been observed to tolerate temperatures ranging from about 7 C to about 40 C and are suitable for USDA Hardiness Zones 8A to 11. In cooler zones, tubers can be "lifted" prior to first freeze and stored in a cool dry environment to overwinter for re-planting the following spring.

It is claimed:

1. A new and distinct *Caladium* plant named 'THAI STR OF17-1082' as illustrated and described.

* * * * *